United States Patent [19]

Krafft

[11] Patent Number: 5,050,595

[45] Date of Patent: Sep. 24, 1991

[54] THERAPEUTIC GARMENT

[76] Inventor: Pam Krafft, 70 Pemberwick Rd., Greenwich, Conn. 06831

[21] Appl. No.: 388,581

[22] Filed: Aug. 1, 1989

[51] Int. Cl.⁵ .............................................. A61F 7/00
[52] U.S. Cl. ................................. 128/379; 128/402; 450/55; 450/69; 450/38
[58] Field of Search ............... 128/379, 402, 403, 399, 128/400, 380; 62/259.3; 450/1, 38, 69, 55; 219/211; 126/204; 165/46; 2/65

[56] References Cited

U.S. PATENT DOCUMENTS

| Re. 14,024 | 11/1915 | Whitmarsh | 128/402 |
|---|---|---|---|
| D. 243,722 | 3/1977 | Poirier | 450/1 |
| 2,298,361 | 10/1942 | Freund | 128/402 |
| 2,853,077 | 9/1958 | Hunau | 450/69 |
| 2,897,821 | 8/1959 | Lerner | 450/55 |
| 3,430,632 | 3/1969 | James et al. | 450/1 |
| 3,500,832 | 3/1970 | Nunnery | 128/379 |
| 3,780,535 | 12/1973 | Spencer | 62/530 |
| 3,995,621 | 12/1976 | Fletcher et al. | 128/379 |
| 4,846,176 | 7/1989 | Golden | 128/400 |

FOREIGN PATENT DOCUMENTS

| 263041 | 4/1988 | European Pat. Off. | 128/402 |
|---|---|---|---|
| 2848088 | 5/1980 | Fed. Rep. of Germany | 128/402 |
| 821150 | 11/1937 | France | 128/402 |

Primary Examiner—Edward M. Coven
Assistant Examiner—Mark S. Graham
Attorney, Agent, or Firm—John R. Doherty

[57] ABSTRACT

A women's therapeutic support garment comprising a pair of breast supporting cups each of which is formed with an inner and an outer panel defining therebetween one of two cupped shaped pockets. A cupped shaped, thermal gel pack is placed in each pocket and has a central opening for accommodating the women's nipple. A pair of side panels are connected to the breast supporting cups, the side panels being dimensioned and configured to encircle the wearer and hold the breast supporting cups in place with the gel packs surrounding the women's breasts. The heat from each gel pack serves to reduce swelling and tenderness of the breast tissues during the premenstrual period, pregnancy or the post-partum period.

15 Claims, 4 Drawing Sheets

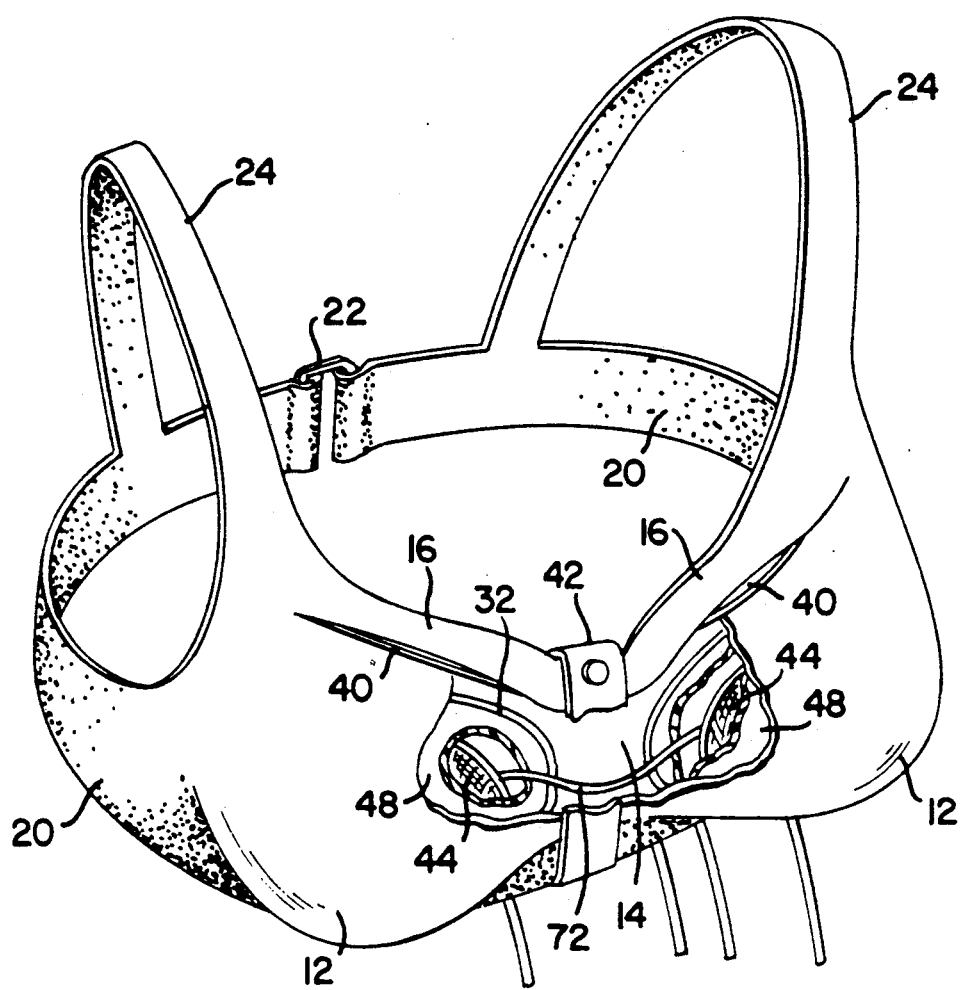
FIG. 7
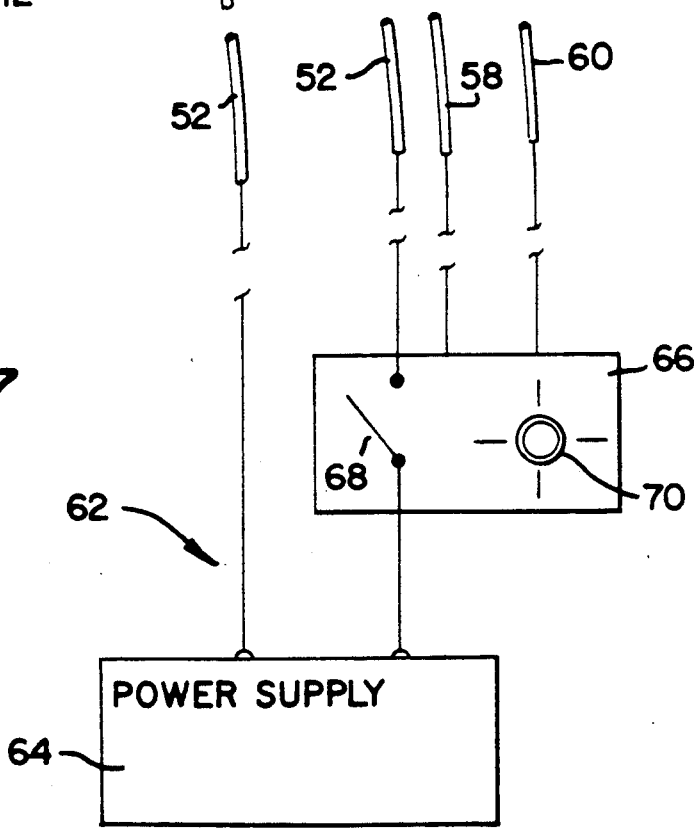

THERAPEUTIC GARMENT

BACKGROUND OF THE INVENTION

This invention relates to women's support garments in general and more particularly to a therapeutic brassiere or bra for use particularly during a women's premenstrual period.

During premenstrual syndrome, pregnancy and the post-partum period, most women suffer the discomforts of swelling and tenderness of the breasts and surrounding tissues due to fluid retention or lactation. A brassiere or bra capable of providing a gentle and even support of the breast tissues can help relieve these discomforts to a great extent. However, most bras tend to cut or provide an uneven pressure on delicate tissue and can cause additional discomfort. Many times doctors will recommend the application of heat to sooth the patient and relieve tenderness. The problem, however, is that most heating pads do not fit well around the breasts and so provide only partial relief. Moreover, the heating pads limit movement of the patient to the length of the electrical cords.

A number of therapeutic wraps or pads employing hot or cold media are known in the prior art. For example, U.S. Pat. No. 4,372,318 to Viesturs et al. discloses an eye pad with two pockets for holding hot or cold water. U.S. Pat. No. 4,676,247 to Van Cleve discloses a thermal wrap employing heated gel packs which is useful in the treatment of injured joints and/or limbs. Until now, however, there has been no provision for a therapeutic support garment, e.g. a brassiere or bra, employing heated gel packs for treating the discomforts of swelling and tenderness occuring during a women's premenstrual or similar periods.

SUMMARY OF THE INVENTION

The invention is directed to a women's therapeutic support garment comprising a pair of breast supporting cups each of which is formed with an inner and an outer panel defining therebetween one of two cupped shaped pockets. A cupped shaped, thermal gel pack is placed in each pocket and has a central opening for accommodating the women's nipple. A pair of side panels are connected to the breast supporting cups, the side panels being dimensioned and configured to encircle the wearer and hold the breast supporting cups in place with the gel packs surrounding the women's breasts. The heat from each gel pack serves to reduce swelling and tenderness of the breast tissues during the premenstrual period, pregnancy or the post-partum period.

BRIEF DESCRIPTION OF THE DRAWINGS

In the accompanying drawings:

FIG. 7 is a perspective view of the brassiere shown in FIG. 4 with part being broken away to show details of construction and also showing a circuit for supplying electrical current to the heating element.

DESCRIPTION OF THE PREFERRED EMBODIMENTS

Figure 1:
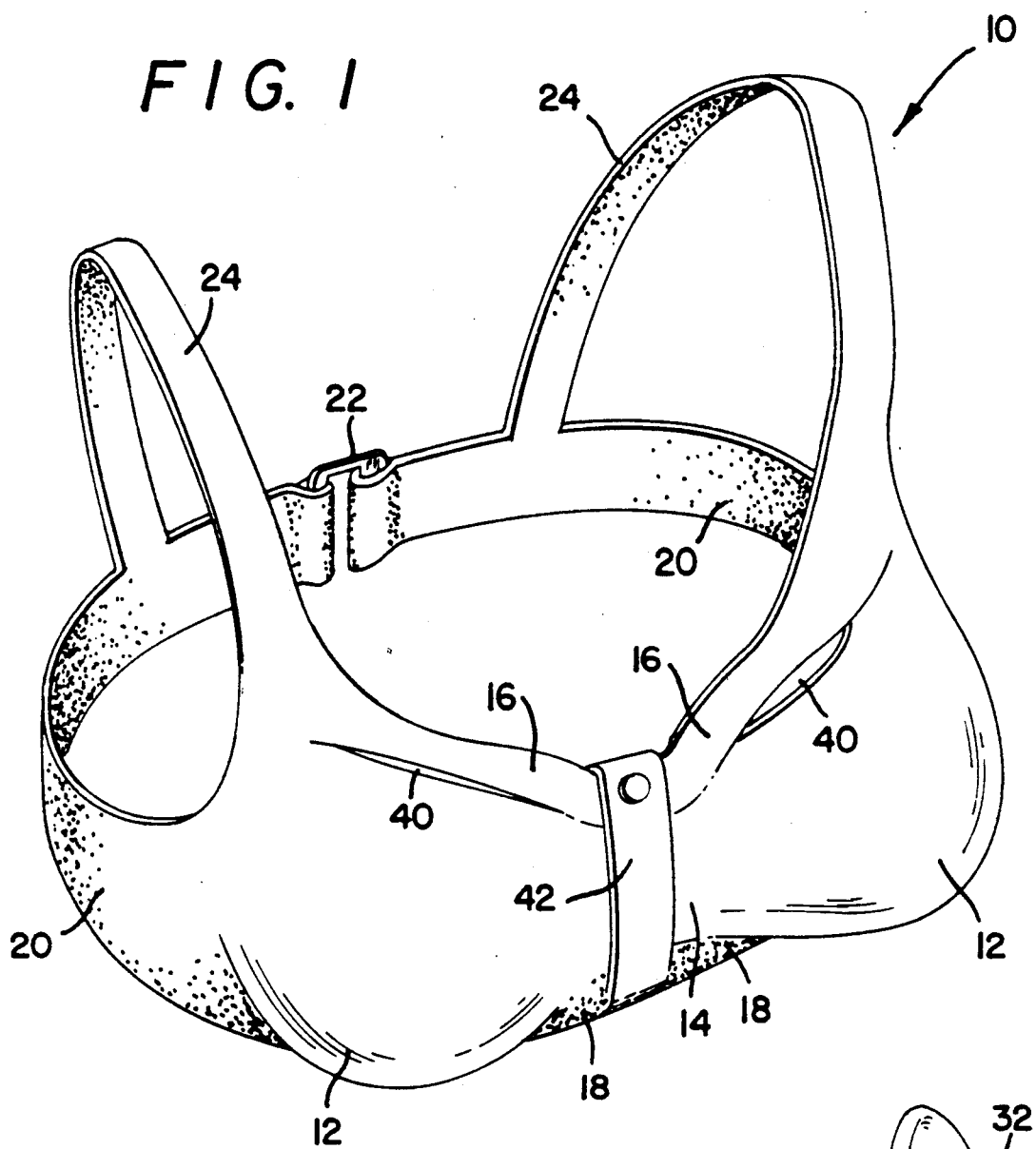
FIG. 1 is a perspective view of a therapeutic brassiere according to the invention.

A brassiere 10 according to the invention includes a pair of three-dimensional bust cups 12, 12 for receiving and supporting a women's breast. The bust cups 12, 12 are permanently secured together at the front of the garment by a front panel 14 and are supported by upper and lower bust bands 16, 18, respectively. The cups are further supported and held in place by a pair of side panels 20, 20, one of each of which is connected to each cup 12, 12. The side panels 20, 20 are dimensioned and configured to encircle the wearer's back and are removably attached to one another by fastening means such as a U-shaped clip 22. A pair of shoulder straps 24, 24 extend between the two upper bust bands 16, 16 and the rear portion of each side panel 20, 20 and provide added support for the garment.

It will be understood that the invention is equally applicable to various other types of garments including strapless and front opening bras. The invention is also applicable to garments other than brassieres such as nightgounds, dresses and the like.

Figure 3:
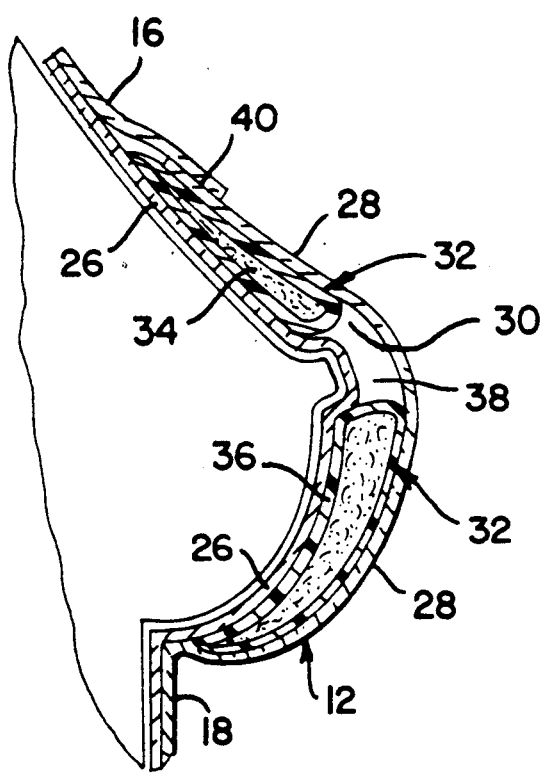
FIG. 3 is a cross-sectional view of the bust cup employed in the brassiere of FIG. 1.

The two bust cups 12, 12 are dimensioned and configured to receive the women's breast and are each made with two layers or panels, i.e., an inner panel 26 and an outer panel 28, (see FIG. 3). The panels form between them pockets 30, 30 for receiving one of two preheated, thermal gel packs 32, 32. Each gel pack is generally conically shaped and includes a heat-retaining gelatinous medium 34. The gel medium 34 is enclosed within an outer liquid impermeable, heat conducting envelope 36. The envelope 36 may be made of a flexible plastic film such as polyethylene, for example.

Figure 2:
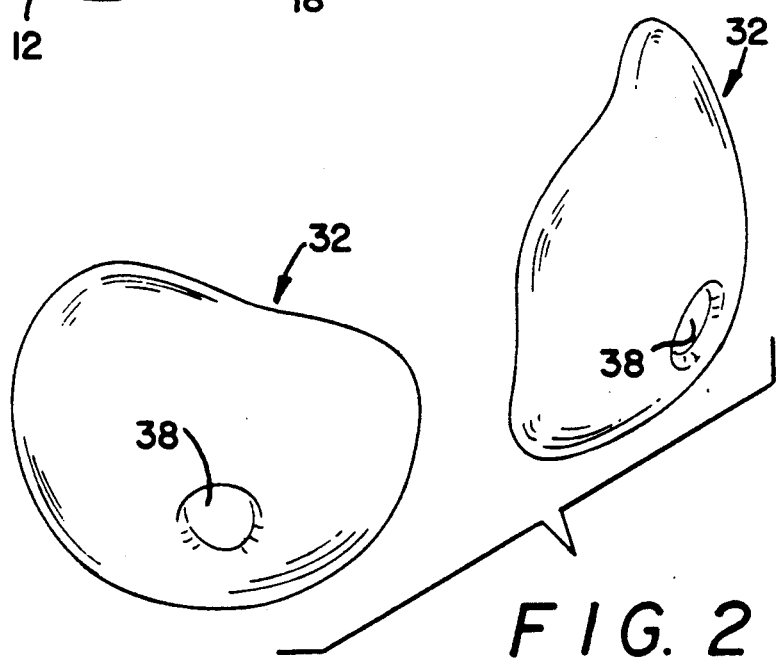
FIG. 2 is a similar view of two thermal gel packs used in the brassiere shown in FIG. 1.

As more particularly shown in FIG. 2, the conical gel packs 32, 32 are formed with central openings 38, 38 in order to accomodate the women's nipple area. The size of the openings should be such as to preclude the heated gel packs 32, 32 from contacting this very sensitive area of the women's body.

In the embodiment of the invention illustrated in FIGS. 1–3, the lower edge of each upper bust band 16, 16 is left free or unconnected so as to form two elongated slots 40, 40 for inserting the heated gel packs into the pockets 30, 30. The upper bands 16, 16 are also preferably made wide enough to overlap the slots and thus provide closures for the two pockets.

It will be seen that the pair of gel packs 32, 32 can be easily inserted through the slots 40, 40 into the two pockets 30, 30 of the bust cups and then just as easily removed after they have cooled down and require reheating again. The gel packs can be heated in warm water or in a microwave oven, for example.

The heat from the gel packs 32, 32 when placed in the cups 12, 12 reduces swelling and tenderness of the breast tissues and relieves the discomforts occuring with the onset of a women's premenstrual period or during pregnancy or the post-partum period. Additional relief and comfort can be provided if the side panels 20, 20 are made to an exceptionally large width (e.g., 2 inches or more) in order to provide support to adjacent tissues and to help ease the back pain that can accompany swelling of the women's breast.

An adjustable tie strap 42 may also be wrapped around the central panel 14 connecting the two cups 12, 12 as shown in FIG. 1. The tie strap 42 allows the wearer to adjust the tightness of the cups around the breast for the maximum therapeutic effect and comfort.

Although not shown in the drawing, the slots for inserting the gel cups may also be formed along the rear panel 26 instead of along the front panel 28 as shown in FIGS. 1 and 3.

FIGS. 4-7, inclusive, illustrate another embodiment of the invention wherein the gel packs 32, 32 are automatically maintained at a preselected temperature by placing electrical heating elements 44, 44 in the cup pockets 30, 30. The heating elements are preferably conical or cupped shaped and are of such size as to fit snugly against each gel pack 32, 32 on the side facing away from the women's breast. The heating elements may be made of a woven, electrically conductive fabric such as graphite cloth, for example.

The cupped shaped heating elements 44, 44 are also preferably formed with central openings 46, 46 which align with the openings 38, 38 in the two gel packs. The former, however, are preferably made larger in diameter than the two openings 38, 38 again to preclude contact with the women's nipple area.

Each of the heating elements 44, 44 is enclosed within a sealed, electrically insulating, heat conducting envelope 48, 48. The envelopes may be made from any electrically non-conductive plastic film material having good heat conducting properties, e.g. polyethylene. The plastic film is sealed around the periphery of each heating element as by a heat seal 50, for example.

An electrical lead 52, 52 is connected to the heating element 44, 44 in each cup pocket 30, 30 and extends outwardly through the peripheral seal 50 of each envelope 48, 48. The leads 52, 52 then protrude through the lower bust bands 18, 18 formed by joining the inner and outer panels 26 and 28 of each cup 12.

A thermal sensor 54 is placed inside at least one of the cup pockets 30, 30 in order to monitor the temperature of the gel packs. The thermal sensor 54 is preferably placed in contact with the side of the gel pack 32 which faces toward the women's breast. This construction insures that the sensor monitors the temperature of the gel pack rather than that of the heating element 44.

The thermal sensor 54 is also enclosed within an outer electrically insulating, heat conducting envelope 56. The envelope 56 may be made of the same electrically non-conductive film plastic material as used for the heating elements 44, 44.

Figure 6:
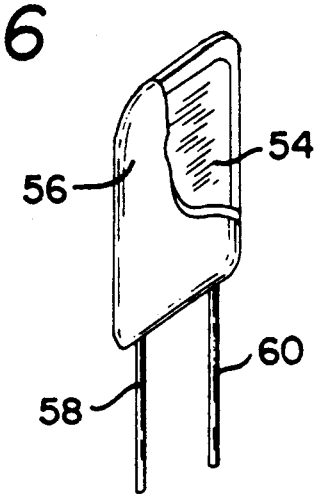
FIG. 6 is a similar view of a thermal sensor employed in the brassiere of FIG. 4.
Figure 4:
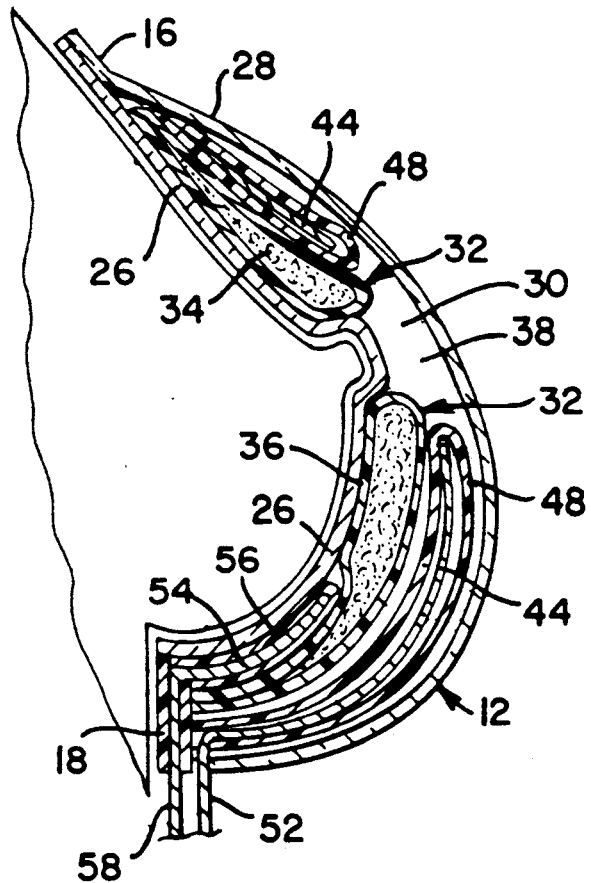
FIG. 4 is a view similar to FIG. 3 showing a different embodiment of a therapeutic brassiere according to the invention.
Figure 5:
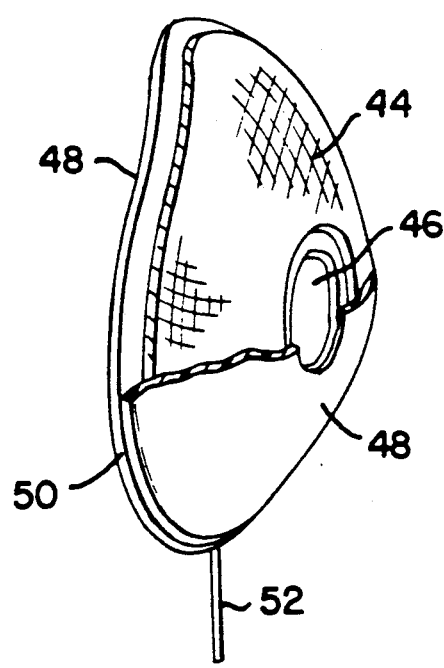
FIG. 5 is a perspective view an electrical heating element employed in the brassiere of FIG. 4.

The thermal sensor 54 is of a conventional type providing a voltage which varies with its temperature. A pair of electrical leads 58, 60 extend outwardly from the envelope 56 as shown in FIG. 6.

An electrical circuit 62 is provided for automatically controlling the temperature of the gel packs 32, 32 in each cup 12, 12 as shown in FIG. 7. The circuit includes a power supply 64 and an adjustable control unit 66 including a switch 68 and a control knob 70. Both the power supply 64 and the control unit 66 may be carried around the user's waist on a belt or attached to a garment or even carried inside a pocket. The power supply, in this case, may be a portable DC battery pack, e.g., rechargeable alkaline batteries, and should have a capacity sufficient to heat the heating elements 44, 44.

The leads 52, 52 extending from the cups 12, 12 are connected to the terminals of the power supply 64 and carry electrical current to each one of the heating elements 44, 44. A small, flexible, insulated conductor 72 bridges across the central panel 14 of the bra and electrically connects the two heating elements 44, 44 to complete the circuit.

The leads 58, 60 from the thermal sensor 54 are connected to the control unit 66 and provide a voltage signal representing the temperature of the heating elements 44, 44. Since essentially the same heating current is fed to both of the heating elements which are connected in series via the conductor 72, the temperature of each element as well as the gel packs 32, 32 will be approximately the same and consequently only one thermal sensor 54 need be used in one of the cup pockets 30, 30.

One of the two leads 52, 52 extending from the heating elements 44, 44 is connected to the switch 68 in the control unit 66 which periodically opens and closes the circuit leading from the power supply 64 in response to changes in the voltage signal from the sensor 54. The operating temperature of the heating elements can be easily preselected by adjusting the knob 70 on the control unit 66 which in turn sets a rheostat (not shown) including the switch 68 or other similar device.

Although the fabric used to construct a therapeutic brassiere according to the invention may be selected from a great variety of materials, it is preferred to employ a soft, flexible, elastic fabric which will stretch in two directions, i.e., a stretch fabric made with bi-directional elastomers. A bra made with this fabric will apply pressure more evenly against the women's breasts for maximum therapeutic effect and comfort. Preferably, at least one of the inner or outer panels 26, 28 forming the cups 12, 12 and both of the side panels 20, 20 are made of this elastic fabric. It is most preferred, however, to employ this fabric for all parts of the bra.

It will be understood, of course, that many modifications of the therapeutic bra or support garment described herein are possible and can be adopted without departing from the spirit and scope of the invention. For example, it is entirely possible to operate the control circuit using AC power with a conventional DC converter instead of the portable battery pack described above as will readily occur to those skilled in the art.

What is claimed is:

1. A women's support garment comprising, in combination:

a pair of breast supporting cups each of which is formed with an inner and an outer panel defining therebetween one of two cupped shaped pockets;

two cupped shaped, thermal gel packs positioned one in each of said pockets, said gel packs each having a central opening for accommodating the nipple area of the women's breast;

an electrical heating element placed within each of said pockets adjacent to a respective one of said thermal gel packs, circuit means for supplying electrical current to said heating elements;

a thermal sensor placed within at least one of said pockets for sensing the temperature of a respective one of said gel packs; and two side panels each one of which is connected to one of said breast supporting cups, said side panels being dimensioned and configured to encircle the wearer and hold said cups in place with said gel packs surrounding the women's breast, the heat from each gel pack serving to reduce swelling of the breast tissues.

2. A women's support garment according to claim 1 wherein said thermal sensor is enclosed within an electrically insulating, heat conducting envelope.

3. A women's support garment according to claim 2, wherein said enclosed thermal sensor is placed adjacent to the side of its respective one of said gel packs facing toward the women's breast.

4. A women's support garment according to claim 3, wherein an adjustable thermostatic switch is provided for opening and closing said circuit in response to changes in the temperature of said thermal sensor.

5. A women's support garment according to claim 4, wherein said circuit includes a portable power supply.

6. A women's support garment comprising, in combination:
- a pair of breast supporting cups each of which is formed with an inner and an outer panel defining therebetween one of two cupped shaped pockets, each of said cups having an opening communicating with one of the pockets formed by said inner and outer panel, at least one of said inner and outer panel being composed of a soft, flexible, elastic fabric stretchable in two directions:
- two cupped shaped, thermal gel packs one of each of which is inserted through said opening and positioned in one of said pockets, said gel packs each having a central opening for accommodating the nipple area of the women's breast;
- an electrical heating element within each of said pockets adjacent to a respective one of said thermal gel packs, said heating element being composed of a woven, flexible, cupped shaped, electrically conductive fabric having a central opening for accommodating the nipple area of the women's breast,
- circuit means for supplying electrical current to said heating element;
- means for adjusting the tightness of said cups around the women's breast; and
- two side panels composed of said soft, stretchable fabric each one of which is connected to one of said breast supporting cups, said side panels being dimensioned and configured to encircle the wearer and hold said cups in place with said gel packs surrounding the women's breast, said side panels being wide enough to support the tissues adjacent to said breast and thereby ease the back pain caused by the swelling of said breast.

7. A women's support garment according to claim 6, wherein at least one of said heating elements is enclosed within an electrically insulating, heat conducting envelope.

8. A women's support garment according to claim 7, wherein said enclosed heating element is placed adjacent to the side of a respective one of said gel packs facing away from the women's breast.

9. A women's support garment comprising, in combination:
- a pair of breast supporting cups each of which is formed with an inner and an outer panel defining therebetween one of two cupped shaped pockets, each of said cups having an opening communicating with one of the pockets formed by said inner and outer panel, at least one of said inner and outer panel being composed of a soft, flexible, elastic fabric stretchable in two directions:
- two cupped shaped, thermal gel packs one of each of which is inserted through said opening and positioned in one of said pockets, said gel packs each having a central opening for accommodating the nipple area of the women's breast;
- an electrical heating element within each of said pockets adjacent to a respective one of said thermal gel packs;
- circuit means for supplying electrical current to said heating element;
- a thermal sensor within at least one of said pockets for sensing the temperature of a respective one of said gel packs;
- means for adjusting the tightness of said cups around the women's breast; and
- two side panels composed of said soft, stretchable fabric each one of which is connected to one of said breast supporting cups, said side panels being dimensioned and configured to encircle the wearer and hold said cups in place with said gel packs surrounding the women's breast, said side panels being wide enough to support the tissues adjacent to said breast and thereby ease the back pain caused by the swelling of said breast.

10. A women's support garment according to claim 9, wherein said thermal sensor is enclosed within an electrically insulating, heat conducting envelope.

11. A women's support garment according to claim 10, wherein said enclosed thermal sensor is placed adjacent to the side of its respective one of said gel packs facing toward the women's breast.

12. A women's support garment according to claim 11, wherein an adjustable thermostatic switch is provided for opening and closing said circuit in response to changes in the temperature of said thermal sensor.

13. A women's support garment according to claim 12, wherein said circuit includes a portable power supply.

14. A women's support garment according to claim 9, wherein each of said heating elements is enclosed within an electrically insulating, heat conducting envelope.

15. A women's support garment according to claim 14, wherein each of said enclosed heating elements is placed adjacent to the side of its respective one of said gel packs facing away from the women's breast.

* * * * *